(12) United States Patent
Seebach et al.

(10) Patent No.: US 6,307,076 B1
(45) Date of Patent: Oct. 23, 2001

(54) PROCESS FOR PREPARING AMIDO PHENYL ESTERS

(75) Inventors: Michael Seebach, Hattersheim; Peter Naumann, Taunusstein; Uwe Bäumler, Frankfurt, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/481,662

(22) Filed: Jan. 12, 2000

(51) Int. Cl.$^7$ .................................................. C07C 231/00
(52) U.S. Cl. .............................................. 554/68; 510/108
(58) Field of Search ................................ 554/68; 510/108

(56) References Cited

U.S. PATENT DOCUMENTS 5,523,434 * 6/1996 Burns et al. .

FOREIGN PATENT DOCUMENTS

WO 94/28106  12/1994  (WO) .
WO 96/39378 * 12/1996  (WO) .

OTHER PUBLICATIONS

EPO Search Report.

* cited by examiner

Primary Examiner—Deborah D. Carr
(74) Attorney, Agent, or Firm—Scott E. Hanf

(57) ABSTRACT

Process for the preparation of amido phenyl esters by reacting an amido acid with an inorganic acid chloride in the melt and reacting the resulting amidocarboxylic acid halide with a phenol derivative in an organic solvent.

12 Claims, No Drawings

PROCESS FOR PREPARING AMIDO PHENYL ESTERS

BACKGROUND OF THE INVENTION

Amido phenol esters are used as bleach activators in detergents and cleaners. They permit a bleaching action even at temperatures below 60° C. by reacting with a source of hydrogen peroxide—in most cases perborates or percarbonates—to release an inorganic peroxy acid.

The patent literature describes various synthesis processes for these bleach activators.

For example, U.S. Pat. No. 5,523,434 describes the preparation of amido phenyl esters from amidocarboxylic acids and phenol sulfonates by a two-stage process: in the first step an amidocarboxylic acid chloride is synthesized by reacting the amidocarboxylic acid with inorganic acid chlorides and, in a second step, the amidocarboxylic acid chloride is reacted with a phenol sulfonate in a water/diethyl ether mixture. A problem for the large-scale applicability of this process is the use of diethyl ether as solvent. Further disadvantages are low yields and the use of large excesses of inorganic acid chloride in the synthesis of the amidocarboxylic acid dichloride.

U.S. Pat. No. 5,466,840 likewise describes a multistage synthesis process for amido phenyl ester sulfonates. In the process, the alkali metal salt of a 4-hydroxybenzenesulfonic acid is reacted with a $C_2$–$C_4$-carboxylic anhydride to give the alkali metal salt of a 4-acyloxybenzenesulfonic acid. The latter is converted, in the second step, to the amido phenyl ester sulfonate by adding 1-oxyalkanoylaminocarboxylic acid in the presence of a transesterification catalyst at from 150 to 250° C. over the course of from 0.5 to 10 hours. The formation of byproducts, losses in yield and complex procedures for purifying the products raise the price of the preparation of this class of substance, used as bleach activators in detergents and cleaners.

In the process according to WO 96/39378, amidocarboxylic acid and a phenol derivative are initially introduced into sulfolane, a carboxylic anhydride, for example acetic anhydride, is added dropwise and, by heating to about 170° C., the conversion to amido phenyl ester sulfonates is achieved over the course of from 0.5 to 10 hours, depending on the starting compound.

Unsatisfactory aspects are the very high energy expenditure while carrying out the reaction, reduced yields, heavily contaminated products, and the very complex and cost-intensive removal of the high-boiling solvent and a very complex recycling of waste gases, byproducts and solvents. The object was therefore to find an improved procedure for preparing amido phenyl ester sulfonates.

It has been found that the slow dropwise addition of an acid halide at from 20 to 130° C. to a solvent-free melt of amidocarboxylic acid and a further reaction of the degassed intermediate amidocarboxylic acid halide with anhydrous phenol sulfonate or a phenol derivative, suspended in a polar, aprotic solvent, at from 20 to 130° C. gives amido phenyl ester sulfonates in very pure form and in high yields. Advantages include a significantly lower expenditure of energy than for current processes, simple removal of the solvent by precipitation of the product, solvent-free and thus readily reusable waste gases, and a reduction in byproducts, in particular in salts.

SUMMARY OF THE INVENTION

The invention relates to the synthesis of amido phenyl esters by reacting amidocarboxylic acids with inorganic acid halides and, in a further reaction step, with a phenol derivative.

The invention provides a process for synthesizing amido phenyl esters of the formula I

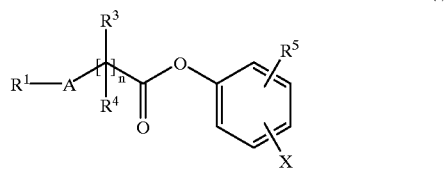

where
A is a group of the formula —$CONR^2$— or —$NR^2CO$—,
$R^1$ is $C_1$–$C_{26}$-alkyl, $C_2$–$C_{26}$-alkenyl, $C_2$–$C_{26}$-alkynyl or $C_3$–$C_8$-cycloalkyl or an aryl or alkylaryl group each having from 6 to 14 carbon atoms,
$R^2$ is hydrogen or $C_1$–$C_{26}$-alkyl, $C_2$–$C_{26}$-alkenyl, $C_2$–$C_{26}$-alkynyl or $C_3$–$C_8$-cycloalkyl or an aryl or alkylaryl group each having from 6 to 14 carbon atoms,
$R^3$ and $R^4$, which can be identical or different, are each hydrogen or $C_1$–$C_{10}$-alkyl, $C_2$–$C_{10}$-alkenyl, $C_2$–$C_{10}$-alkynyl or $C_3$–$C_8$-cycloalkyl,
$R^5$ is hydrogen, halogen or $C_1$–$C_6$-alkyl, $C_2$–$C_6$-alkenyl, $C_2$–$C_6$-alkynyl, $C_3$–$C_8$-cycloalkyl or $C_1$–$C_6$-alkoxy, n is a number from 1 to 10, X is a group of the formulae $SO_3M$, $OSO_3M$, $(CH_2)_mSO_3M$, $(CH_2)_mOSO_3M$, $CO_2M$ and $N(R^6)_3Y$,
where M is hydrogen or an alkali metal ion,
$R^6$ is an alkyl group having from 1 to 6 carbon atoms or a cycloalkyl group having from 3 to 8 carbon atoms,
Y is a halogen atom and
m is 1 or 2.

DESCRIPTION OF THE PREFERRED EMBODIMENTS

Preference is given to the preparation of compounds of the formula (I) where, at the same time, A is a group of the formula —$CONR^2$—, $R^1$ is $C_6$–$C_{10}$-alkyl, $R^2$, $R^3$, $R^4$ and $R^5$ are hydrogen, n=5 and X is —$SO_3M$.

This process comprises adding an inorganic acid halide to a melt of the compound of the formula ll

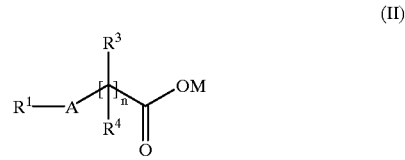

freeing the resulting amidocarboxylic acid halide under reduced pressure from waste gases which remain, and reacting this amidocarboxylic acid halide in a second reaction step with a phenol derivative of the formula III

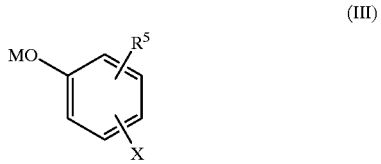

suspended in a suitable organic solvent.

In the first reaction stage, the compound of the formula I is melted, and an inorganic acid halide is slowly added dropwise to the melt with stirring.

The organic acid halide can, for example, be $PCl_3$, $PCl_5$, $POCl_3$, $COCl_2$, preferably $SOCl_2$. Instead of these chlorides, it is also possible to use the analogous bromides. The amount of acid halide is from 0.5 to 2, preferably from 0.7 to 1.5, in particular from 0.9 to 1.4, mole equivalents, based on the amidocarboxylic acid. The temperature at which the reaction is carried out is dependent on the melting point of the amidocarboxylic acid and is generally from 20 to 120° C., preferably from 50 to 110° C., particularly preferably from 70 to 100° C. For the first process step the reaction proceeds over a period of from 10 minutes to 5 hours, preferably from 30 minutes to 3 hours, which is followed by a post-stirring time of from 10 minutes to 3 hours, preferably from 30 minutes to 2 hours. When the reaction is complete, the vacuum is applied in order to remove the waste gases which have formed, in particular $SO_2$, HCl, and residues of inorganic acid halides.

In the second reaction step, a melt of the acid chloride obtained in the first process step is initially introduced, and a suspension of the compound III in a suitable solvent is slowly added to this melt under inert gas.

Suitable solvents are, for example, xylene, benzene, monoglyme, diglyme, diisopropyl ether, tetrahydrofuran, dioxane, isobutyl methyl ketone, acetone, diethyl ketone, acetonitrile, fatty acid alkyl esters, preferably $C_2$–$C_4$-alkyl acetates. Examples of these solvents are ethyl acetate, n-propyl acetate, i-propyl acetate, n-butyl acetate, i-butyl acetate, t-butyl acetate or mixtures thereof. Preference is given to n-butyl acetate since this solvent has very good solubility for the starting products and has good crystallization behavior of the end product. The molar ratio of the compounds of the formulae II and III is from 1:0.7 to 1.5, preferably 1:0.8 to 1.3.

The reaction time in the second process step is from approximately 1 minute to 2 hours, preferably from 15 to 90 minutes. This is followed by a post-stirring time of from 1 minute to 2 hours. The reaction temperature in the second stage is generally from 15 to 110° C.

The reaction mixture is, following dilution with water, adjusted to a pH of from pH 4 to pH 11, preferably from pH 7 to pH 10, by adding a base, preferably sodium hydroxide solution, potassium hydroxide solution, sodium carbonate or potassium carbonate. The resulting end products can be separated off from this mother liquor by filtration, filtration with suction, decantation or by centrifugation. For purification, the moist product can be stirred with or recrystallized from water, alcohols, aromatic solvents, alkanes, ketones or esters, and mixtures of these, preferably with water, alcohols or esters or mixtures thereof.

In the synthesis process according to the invention, the target compound is obtained in yields greater than 80% and a high purity (content of amido phenyl ester greater than 90%).

The examples below serve to illustrate the invention in more detail without limiting it thereto.

EXAMPLE 1

135.7 g (0.5 mol) of n-nonanoylamidohexanoic acid were initially introduced and melted at a temperature of from 85° C. to 90° C. 59.5 g (0.5 mol) of thionyl chloride were metered into the melt over the course of 2 hours. The reaction mixture was then stirred for 1 hour at room temperature and degassed in a water-pump vacuum for a period of 1.5 hours. The resulting n-nonanoylamidohexanoyl chloride was heated to from 85° C. to 90° C., and 100.1 g (0.5 mol) of anhydrous p-phenolsulfonic acid, sodium salt, suspended in 300 ml of n-butyl acetate, were metered in over the course of 1 hour under a nitrogen atmosphere. The reaction mixture was then stirred for 1 hour at from 85 to 90° C.

After the mixture had been cooled to about 30° C., 900 ml of water were added with vigorous stirring. 128 g of sodium hydroxide solution (32% strength) were added dropwise at a temperature of from 35 to 40° C. to adjust the pH to 8.0. The product which precipitated out was cooled to 20° C. and filtered off with suction, washed once with water and dried overnight at 60° C. in a vacuum drying cabinet.

87% was n-nonanoylamidocaproyloxybenzenesulfonic acid, sodium salt, obtained as a white solid.

EXAMPLE 2

135.7 g (0.5 mol) of n-nonanoylamidohexanoic acid were initially introduced and melted at a temperature of from 85° C. to 90° C. 59.5 g (0.5 mol) of thionyl chloride were metered into the melt over the course of 2 hours. The reaction mixture was then stirred for 1 hour at room temperature and degassed in a water-pump vacuum for a period of 1.5 hours. The resulting n-nonanoylamidohexanoyl chloride was heated to 90° C., and 100.1 g (0.5 mol) of anhydrous p-phenolsulfonic acid, sodium salt, suspended in 300 ml of n-butyl acetate, were metered in over the course of 5 minutes under a nitrogen atmosphere. The reaction mixture was then stirred for 30 minutes at 90° C.

After the mixture had been cooled to about 30° C., 900 ml of water were added with vigorous stirring. 123 g of sodium hydroxide solution (32% strength) were added dropwise at a temperature of from 35 to 40° C. to adjust the pH to 8.0. The product which precipitated out was cooled to 20° C. and filtered off with suction, washed once with water and dried overnight at 60° C. in a vacuum drying cabinet.

86% was n-nonanoylamidocaproyloxybenzenesulfonic acid, sodium salt, obtained as a white solid.

What is claimed is:

1. A process for preparing amido phenyl esters of the formula I

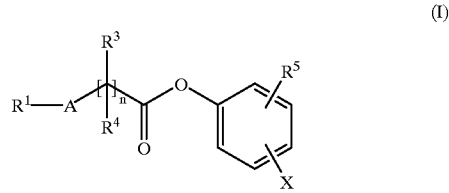

where

A is a group of the formula —$CONR^2$— or —$NR^2CO$—, $R^1$ is $C_1$–$C_{26}$-alkyl, $C_2$–$C_{26}$-alkenyl, $C_2$–$C_{26}$-alkynyl or $C_3$–$C_8$-cycloalkyl or an aryl or alkylaryl group each having from 6 to 14 carbon atoms, $R^2$ is hydrogen or $C_1$–$C_{26}$-alkyl, $C_2$–$C_{26}$-alkenyl, $C_2$–$C_{26}$-alkynyl or $C_3$–$C_8$-cycloalkyl or an aryl or alkylaryl group each having from 6 to 14 carbon atoms, $R^3$ and $R^4$, which can be identical or different, are each hydrogen or $C_1$–$C_{10}$-alkyl, $C_2$–$C_{10}$-alkenyl, $C_2$–$C_{10}$-alkynyl or $C_3$–$C_8$-cycloalkyl, $R^5$ is hydrogen, halogen or $C_1$–$C_6$-alkyl, $C_2$–$C_6$-alkenyl, $C_2$–$C_6$-alkynyl, $C_3$–$C_8$-cycloalkyl or $C_1$–$C_6$-alkoxy, n is a number from 1 to 10, X is a group of the formulae $SO_3M$, $OSO_3M$, $(CH_2)_mSO_3M$, $(CH_2)_mOSO_3M$, $CO_2M$ and $N(R^6)_3Y$, where M is hydrogen or an alkali metal ion,
$R^6$ is an alkyl group having from 1 to 6 carbon atoms or a cycloalkyl group having from 3 to 8 carbon atoms,
Y is a halogen atom and
m is 1 or 2,
which comprises adding an inorganic acid halide to a melt of the compound of the formula II

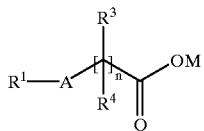

freeing the resulting amidocarboxylic acid halide under reduced pressure from waste gases which remain, and reacting this amidocarboxylic acid halide in a second reaction step with a phenol derivative of the formula III

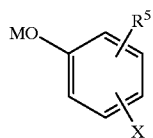

suspended in a suitable organic solvent.

2. The process as claimed in claim 1, wherein the molar ratio of the compounds II and III is from 1:0.7 to 1.5.

3. The process as claimed in claim 1, wherein the molar ratio of the compounds II and III is from 1:0.8 to 1.3.

4. The process as claimed in claim 1, wherein toluene is used as solvent.

5. The process as claimed in claim 1, wherein acetonitrile is used as solvent.

6. The process as claimed in claim 1, wherein a $C_1$–$C_4$-alkyl acetate is used as solvent.

7. The process as claimed in claim 1, wherein n-butyl acetate is used as solvent.

8. The process as claimed in claim 1, wherein the amount of acid halide is from 0.5 to 2 mol equivalents, based on amidocarboxylic acid II.

9. The process as claimed in claim 1, wherein the amount of acid halide is from 0.7 to 1.5 mol equivalents, based on amidocarboxylic acid II.

10. The process as claimed in claim 1, wherein the amount of acid halide is from 0.9 to 1.4 mol equivalents, based on amidocarboxylic acid II.

11. The process as claimed in claim 1, which is carried out at from 25 to 120° C.

12. A detergent or cleaner comprising an amido phenyl ester prepared as claimed in claim 1.

\* \* \* \* \*